(12) United States Patent
Nakagami

(10) Patent No.: US 6,638,254 B2
(45) Date of Patent: Oct. 28, 2003

(54) INDWELLING NEEDLE ASSEMBLY

(75) Inventor: Hiroyuki Nakagami, Osaka (JP)

(73) Assignee: Nipro Corporation, Osaka (JP)

(*) Notice: Subject to any disclaimer, the term of this patent is extended or adjusted under 35 U.S.C. 154(b) by 0 days.

(21) Appl. No.: 09/982,850

(22) Filed: Oct. 22, 2001

(65) Prior Publication Data

US 2002/0055716 A1 May 9, 2002

(30) Foreign Application Priority Data

Oct. 23, 2000 (JP) ........................................ 2000-322423

(51) Int. Cl.$^7$ .............................................. A61M 5/178
(52) U.S. Cl. ........................... 604/164.08; 604/164.01; 604/198
(58) Field of Search ............................. 604/164.01, 44, 604/164.06, 164.08, 510, 158, 164.02, 164.12, 198, 162, 192, 195

(56) References Cited

U.S. PATENT DOCUMENTS 5,562,634 A * 10/1996 Flumene et al. ............ 604/171
6,319,233 B1 * 11/2001 Jansen et al. ................ 604/192
6,475,191 B2 * 11/2002 Tamura et al. ......... 604/164.08

* cited by examiner

Primary Examiner—Brian L. Casler
Assistant Examiner—Lina R Kontos
(74) Attorney, Agent, or Firm—Kubovcik & Kubovcik

(57) ABSTRACT

An indwelling needle assembly having an outer needle to be pieced and retained in tissue of a living body, an outer needle hub to which the outer needle is fixed, an inner needle slidably inserted in a lumen of the outer needle and having a sharp blade edge, an inner needle hub to which the inner needle is fixed, and a needle guard having a multi-tube structure composed of a plurality of telescoping tubes and capable of accommodating the inner needle and the inner needle hub therein. The assembly has a first elastic means provided in the needle guard for withdrawing the tubes, a second elastic means that engages with the inner needle hub and biases the hub toward the proximal end of the guard, and a stopper means that holds the inner needle hub and the needle guard against biasing forces of the elastic means.

6 Claims, 6 Drawing Sheets

INDWELLING NEEDLE ASSEMBLY

TECHNICAL FIELD OF THE INVENTION

The present invention relates to an indwelling needle assembly including an indwelling needle to be temporarily indwelt in a blood vessel for infusion or the like. More specifically, the present invention relates to an indwelling needle assembly where, after an inner needle and an outer needle are simultaneous pierced into tissue of a living body, and the outer needle is retained in the tissue and the inner needle is removed from the outer needle, the inner needle can be safely and readily stored in a needle guard.

BACKGROUND OF THE INVENTION

An indwelling needle used for infusion or the like ordinarily has a double-needle structure composed of an outer needle and an inner needle. Upon its use, the indwelling needle is pierced into a blood vessel in a state where the inner needle is positioned in a lumen of the outer needle. After the outer needle is inserted to a predetermined position, the inner needle is removed from the lumen of the outer needle and an infusion line or the like is connected to a proximal end portion of the outer needle so that an infusion, a liquid medicament or the like is introduced into the blood vessel through the lumen of the outer needle. The outer needle is made of a flexible resin that is unlikely to damage the inside of the blood vessel. The inner needle is generally made of a metal that is easy to insert into the blood vessel.

After the outer needle of the indwelling needle is retained in a body of a patient, the inner needle that is removed from the lumen of the outer needle is disposed of. On this occasion, medical personnel, patients or other persons may be injured by touching the sharp tip of the inner needle. If the tip of the inner needle is protected by a suitable method, the inner needle itself used for a patient suffering from a disease that infects through blood, such as hepatitis or acquired immune deficiency syndrome (AIDS), can be an infection medium, not to speak of the tip itself of the inner needle.

For this reason, it is very important to properly dispose of the inner needle that has been used to pierce a blood vessel of a patient. However, priority is given to treatment of a patient and disposal of inner needles is frequently postponed.

In recent years, indwelling needle assemblies for immediate and easy disposal of inner needles after use (Japanese Patent Application Laid-open Nos. Hei 3-63066, Hei 6-78999, Hei 6-86821, Hei 7-328116, Hei 11-57002, etc.) have been proposed.

These indwelling needle assemblies are composed of a tubular housing having arranged therein an inner needle hub connected to an inner needle and a needle guard slidably arranged between the housing and the inner needle hub and having a catheter connected to a distal end thereof. After removing the inner needle from a lumen of an outer needle of the indwelling needle assembly while retaining the outer needle in a patient, the needle guard is slid toward the distal end of the housing so that the inner needle can be easily accommodated in the needle guard. Since, after removing the inner needle, the inner needle can be easily protected by one hand of a person, these indwelling needle assemblies free the person of the fear that the person will be hurt by the tip of the inner needle or infected with diseases by blood adhered to the inner needle.

However, in each of these indwelling needle assemblies, the needle guard, which is longer than the inner needle, is slid toward the distal end of the housing by the length of the inner needle. Therefore, it is difficult for medical personnel with small hands to completely protect the inner needle by sliding the needle guard using one hand. Further, in the case of medical personnel other than those with small hands, when using a long indwelling needle such as one retained in a femoral vein of the inguinal region at the time of emergency dialysis, it is difficult to slide the needle guard using one hand to a position where the inner needle can be completely protected. Japanese Patent Application Laid-open No. Hei 7-328116 discloses a piercing needle whose needle casing for accommodating an inner needle has a telescopic structure comprising several short tubes. When the indwelling needle is retained in the human body, it is easy for medical personnel with small hands to use it since it has a small size. However, it is still necessary to slide the needle casing toward the distal end of the housing by the length of the inner needle to protect the inner needle removed from the indwelling needle.

On the other hand, taking the above problems in consideration, an indwelling needle assembly has been developed in which a spring is arranged between an inner needle hub and a proximal end portion of a needle guard. When a locking mechanism of a push button type in the indwelling needle assembly is released, the inner needle hub is moved toward the proximal end of the needle guard by the force of the spring (Japanese Patent Application Laid-open Nos. Hei 8-215315 and Hei 9-103492).

However, in the case of indwelling needle assemblies with a push-button type locking mechanism, when a long indwelling needle such as the one described above is used, it takes a certain time for the inner needle to be accommodated in the needle guard. As a result, there is increased fear that medical personnel will be hurt by the tip of the inner needle or infected with diseases by blood adhered to the inner needle. On the other hand, when a strong spring is used to shorten the time necessary for accommodating the inner needle, the hand of a medical person holding the indwelling needle assembly receives a greater impact at the time of accommodating the inner needle and the indwelling needle assembly may be dropped or the medical personnel may feel anxiety because of the impact. Also, there is a fear that the impact may cause scattering of the blood that remains inside the inner needle.

Under the above circumstances, an object of the present invention is to provide an indwelling needle assembly in which an inner needle of the indwelling needle can be easily accommodated in a needle guard by one hand without receiving a strong impact which may cause medical personnel to feel uneasy if a long indwelling needle is used or if it is used by medical personnel with small hands, and that requires only a short time for accommodating the inner needle and is free of the fear of blood scattering.

SUMMARY OF THE INVENTION

With a view to solving the above-mentioned problems, the inventor of the present invention conducted extensive research. He found an indwelling needle assembly comprised of a needle guard having a multi-tube structure composed of a plurality of telescoping tubes, a first elastic body for extending the needle guard and, a second elastic body for drawing an inner needle hub into the needle guard. As a result, there is a shortened time for accommodating the inner needle in the needle guard in the indwelling needle assembly as compared with the time of a conventional indwelling needle assembly and a small impact is given to the hand that holds the indwelling needle assembly. The present invention has been achieved based on this discovery.

That is, the present invention provides an indwelling needle assembly characterized as comprising an outer needle to be pierced into and retained in a tissue of a living body, an outer needle hub having a distal end portion to which the outer needle is fixed, an inner needle slidably inserted in a lumen of the outer needle and having a sharp blade edge at a distal end portion thereof, an inner needle hub having a distal end portion to which the inner needle is fixed, a needle guard of a multi-tube structure which is composed of a plurality of telescoping tubes and is capable of accommodating the inner needle and the inner needle hub therein, a first elastic means provided on the needle guard for extending the plurality of telescoping tubes so as to extend, or lengthen, the needle guard, a second elastic means which engages the inner needle hub and is capable of biasing the inner needle hub toward a proximal end side of the needle guard, and a stopper means capable of holding the inner needle hub and the needle guard against the biasing forces of the first and second elastic means, respectively.

DESCRIPTION OF THE DRAWINGS

Referring to the preferred embodiments and attached drawings, indwelling needle assemblies of the present invention will hereinafter be described. However, the present invention is not limited thereto.

DETAILED DESCRIPTION OF THE INVENTION

Figure 1:
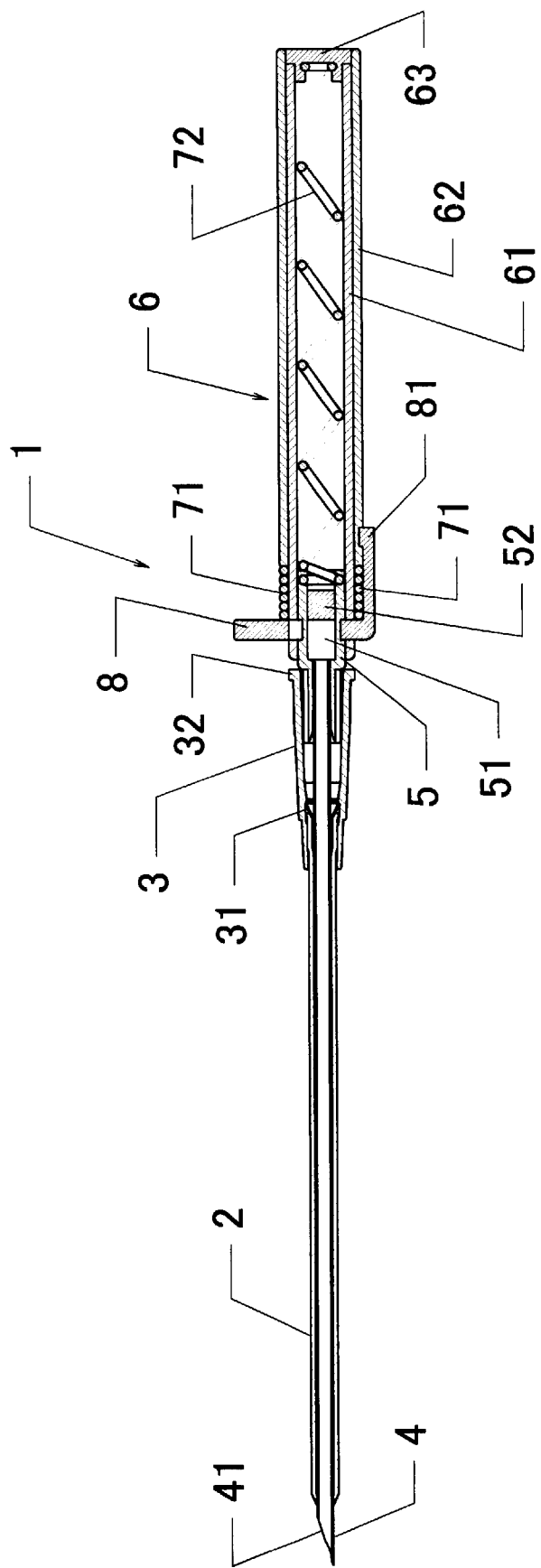
FIG. 1 is a cross-sectional view in the vertical direction of an indwelling needle assembly according to an embodiment of the present invention showing a state before the inner needle is protected.
Figure 2:
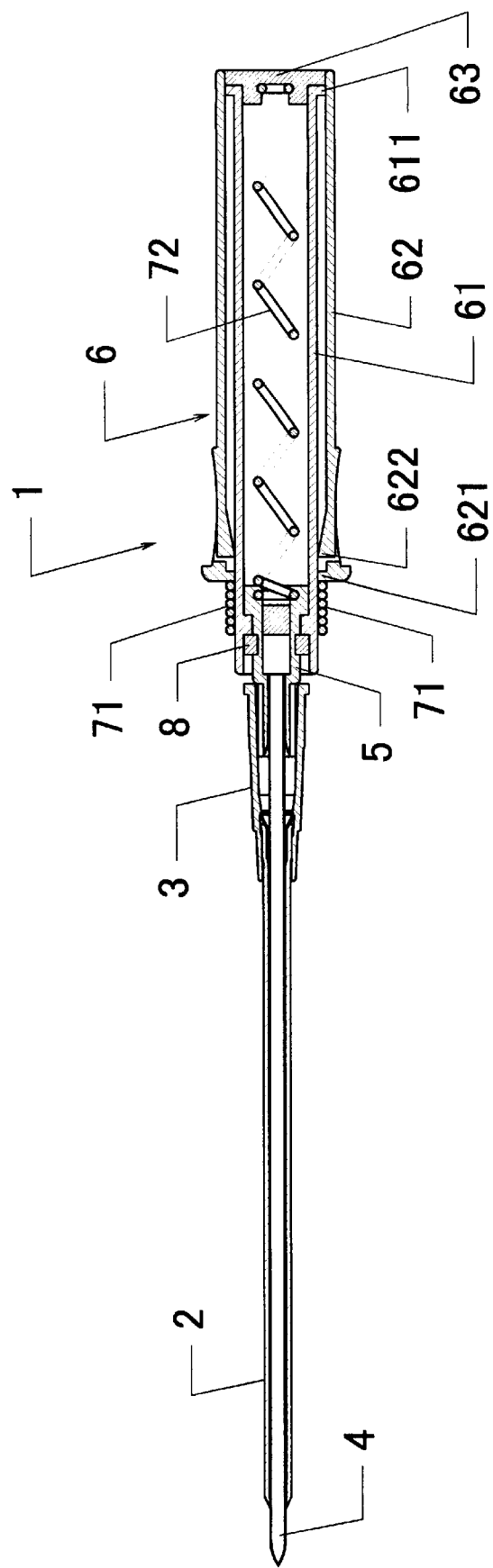
FIG. 2 is a cross-sectional view in the horizontal direction of the indwelling needle assembly shown in FIG. 1.

As shown in FIGS. 1 and 2, an indwelling needle assembly 1 of the present invention has an outer needle 2, an outer needle hub 3 having a distal end portion to which the outer needle 2 is fixed, an inner needle 4 that can be inserted in a lumen of the outer needle 2 and has a sharp blade edge 41 at a distal end portion thereof, an inner needle hub 5 having a distal end portion to which the inner needle 4 is fixed, and a needle guard 6 capable of accommodating the inner needle 4 and the inner needle hub 5 therein.

In relation to the indwelling assembly 1 of the present invention, the term "distal end" means the side which pierces a patient (in the figures, the left side) and the term "proximal end" means the opposite side of the distal end (in the figures, the right side).

Outer needle 2 is a hollow tube and its distal end portion is preferably formed into a tapered shape in which the outer diameter is reduced toward the distal end in order to reduce piercing resistance. Since the outer needle 2 is retained for some time in the body of a patient after its insertion, the outer needle 2 is formed preferably from a flexible resin that has less possibility of hurting the patient. More particularly, the outer needle 2 is formed from ethylene tetrafluoroethylene copolymer, polyurethane, polyether, nylon resin, and the like.

The outer needle 2 may sometimes be broken off by the movement of a patient while it is retained in the body of the patient. In such a case, in order to find fragments of the outer needle 2, an X-ray contrast medium such as barium sulfate may be blended in the material of the outer needle 2 so that the outer needle 2 can have a contrast medium function.

An outer needle hub 3 is fixed to the proximal end portion of the outer needle 2. The method for fixing these components includes a method in which a caulking pin 31 is used for caulking, adhesion using an adhesive, fusion by heat and so forth.

The outer needle hub 3 is a hollow tube and is formed in the form of a taper in which the inner diameter is increased toward the proximal end. The taper form of the outer needle hub ensures a connection between the outer needle hub 3 and a tube of an infusion set or the like. A projection 32 may be provided at the proximal end portion of the outer needle hub 3 for connecting with a lock-type luer tapered part that is provided in a syringe, tube or the like of an infusion set.

As the material of the outer needle hub 3, hard resins such as polyolefin, for example, polyethylene, polypropylene and ethylene-vinyl acetate copolymer, and polyvinyl chloride, polybutadiene, polyamide and polyesters may be used.

Inner needle 4 is a hollow tube that can be inserted into a lumen of the outer needle 2. The outer diameter of the inner needle 4 is set slightly smaller than the inner diameter of the outer needle 2, so that the outer needle 2 is held around the inner needle 4 and there is no fear that the outer needle 2 will come off unless a force is applied from outside.

A sharp blade edge 41 is formed at the distal end portion of the inner needle 4. The blade edge 41 has an inclined blade surface in order to reduce piercing resistance. The inner needle 4 is pierced into a patient in a state in which it is inserted in the outer needle 2. When the indwelling needle assembly 1 is pierced in a patient, the blade edge 41 of the inner needle 4 must protrude from the distal end of the outer needle 2.

The material of the inner needle 4 includes metal materials such as stainless steel, aluminum, titanium, and alloys thereof.

An inner needle hub 5 is fixed to the proximal end portion of the inner needle 4. Similarly to the fixing method for the outer needle 2 and outer needle hub 3, the fixing method therefor includes adhesion using an adhesive, fusion by heat and so forth. As the material of the inner needle hub 5, transparent or translucent hard materials such as polycarbonate, acrylonitrile-butadiene-styrene copolymers, polystyrene, polyethylene and polypropylene are preferably used. This enables confirmation of backflow of blood when the inner needle 4 is pierced into a patient (hereinafter referred to as "flashback").

The inner needle hub 5 has a lumen 51 in communication with a lumen of the inner needle 4. When the inner needle 4 is pierced into the body of a patient, the lumen 51 communicates with outside of the indwelling needle assembly 1 only through a filter 52 provided at the proximal end portion of the inner needle hub 5. The filter 52 allows air to permeate but does not allow blood to permeate therethrough.

More particularly, sintered filters or nonwoven fabrics made of synthetic resins such as polypropylene, polystyrene and polymethyl methacrylate are preferably used. Therefore, when the inner needle 4 and the outer needle 2 are pierced into the blood vessel of a patient, the air in the inner needle 4 and in the inner needle hub 5 is discharged to the outside of the indwelling needle assembly 1 through the filter 52, so that flashback can be confirmed. The blood which flows into the inner needle 4 and the inner needle hub 5 due to the flashback is prevented from leaking to the outside by the filter 52.

After being removed from the lumen of the outer needle 2, the inner needle 4 and inner needle hub 5 are accommodated in needle guard 6. The needle guard 6 has a multi-tube structure composed of a plurality of telescoping tubes. Before the inner needle 4 is accommodated in the needle guard 6, the tubes are used in a state such that they are superposed on each other and the total length of the needle guard 6 is in its shortest state. When the inner needle 4 is accommodated in the needle guard 6, the tubes are extended and they are used in a state such that the total length of the needle guard 6 is in its longest state. As the number of tubes is larger, the total length of the needle guard 6 is shorter before the inner needle 4 is accommodated therein and the impact is smaller at the time of accommodating of the inner needle 4. As a result, the indwelling needle assembly can be used readily by medical personnel. On the other hand, the number of parts increases to make production difficult and also increases the cost. Therefore, it is preferable that the indwelling needle assembly of the present invention is of a double-tube or triple-tube structure composed of two or three tubes.

An embodiment of an indwelling needle assembly 1 having a double-tube structure in which the needle guard is composed of two tubes will be illustrated with reference to FIGS. 1 to 4.

As shown in FIGS. 1 and 2, a needle guard 6 has a double-tube structure composed of two tubes, which are an inner tube 61 and an outer tube 62. The outer diameter of the inner tube 61 is set to be slightly smaller than the inner diameter of the outer tube 62 and the inner tube 61 is slidable with respect to the outer tube 62. As the materials for the inner tube 61 and the outer tube 62, transparent or translucent hard materials such as polycarbonate, acrylonitrile-butadiene-styrene copolymer, polystyrene, polyethylene and polypropylene are preferably used.

A cap member 63 is provided at the proximal end portion of the needle guard 6 in order to prevent blood attached to the inner needle 4 and inner needle hub 5 accommodated in the needle guard 6 from leaking or the user of the indwelling needle assembly 1 from contacting the inner needle 4 and the inner needle hub 5. The cap member 63 is engaged with or fixed to the proximal end portion of the outer tube 62. As the material thereof, the same material as that of the tube that constitutes the needle guard 6 is preferably used.

The needle guard 6 is provided with a first elastic body 71 and a second elastic body 72 for positioning the inner needle hub and the inner needle 4 into the needle guard 6.

The first elastic body 71 is provided on an outer surface of the inner tube 61, and sandwiched between a stopper 8 (cf., FIG. 1) described later and an projection 621 (cf., FIG. 2) that is provided on the distal end portion of the outer tube 62 and is projected inwardly. The first elastic body 71 is urged so that the outer tube 62 is biased toward the proximal end of the inner tube 61. The first elastic body 71 may be fixed to the projection 621 at a proximal end portion thereof.

The second elastic body 72 is arranged between the proximal end of the inner needle hub 5 and the cap member 63 and is urged so that the inner needle hub 5 is biased toward the proximal end of the needle guard 6. The distal end portion of the second elastic body 72 is fixed to the proximal end portion of the inner needle hub 5 and is fixed at the proximal end portion thereof to the distal end portion of the cap member 63.

As the elastic bodies used for the first elastic body 71 and the second elastic body 72, spring steel, an elastomer and so forth can be used. More preferably, spring steel having excellent corrosion resistance is used. The materials of the first elastic body 71 and of the second elastic body 72 may be the same or different.

Here, the term "bias" means having a tendency of moving in one direction.

A mobile stopper 8 is provided on the distal end portion of the needle guard 6. The stopper 8 can engage with the inner needle hub 5 and the needle guard 6, with the result that the inner needle hub 5 and the needle guard 6 can be held in a state against the biasing forces provided by the first elastic body 71 and the second elastic body 72 before the inner needle 4 is protected in the needle guard 6.

As the stopper 8, for example, a latch member having a keyhole may be used. When the inner needle hub 5 is positioned at the distal end portion of the needle guard 6, the latch member 8 is engaged with the inner needle hub 5 through the keyhole and holds the inner needle hub 5 against the biasing force provided by the second elastic body 72.

On the other hand, the latch member 8 is engaged with the outer tube 62 through a stopping part 81 arranged so as to extend along the outer surface of the needle guard 6 toward the proximal end of the needle guard 6. The stopping part 81 holds the needle guard 6 against the biasing force of the first elastic body 71 in a state where the total length of the needle guard 6 is shortest.

Figure 3:
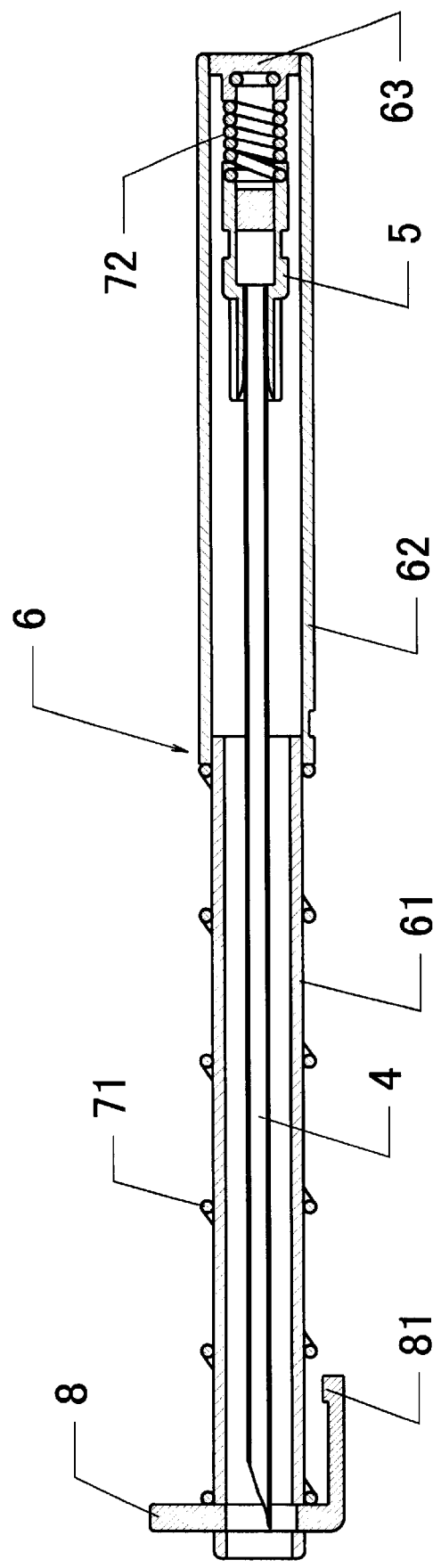
FIG. 3 is a cross-sectional view in the vertical direction of an indwelling needle assembly according to an embodiment of the present invention showing a state after the inner needle is protected.
Figure 4:
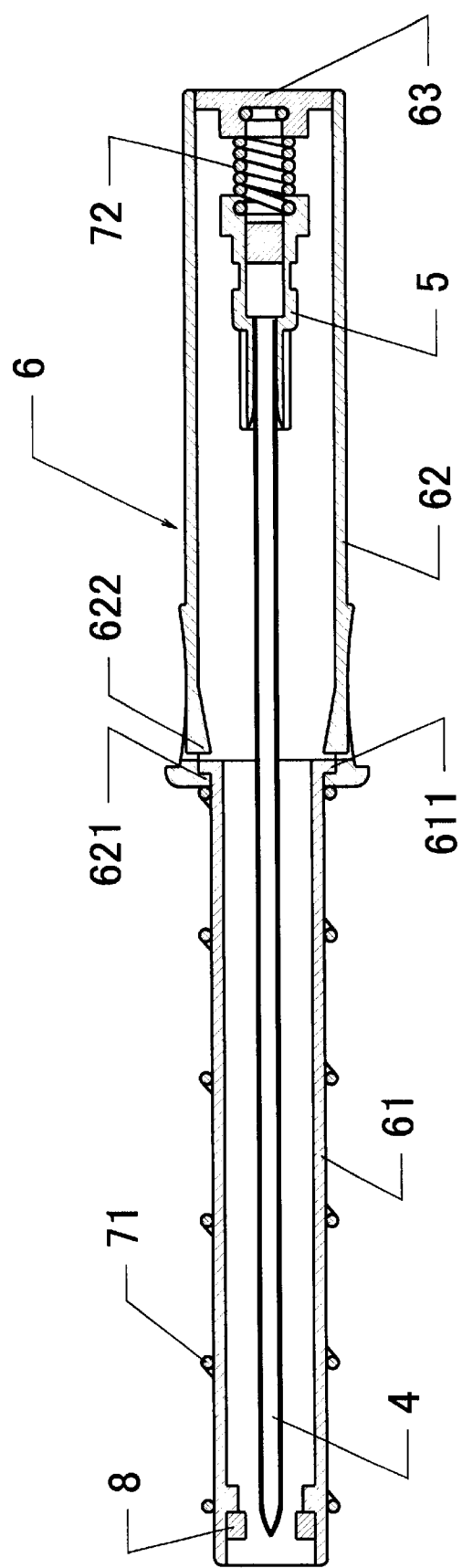
FIG. 4 is a cross-sectional view in the horizontal direction of the indwelling needle assembly shown in FIG. 3.

After medical personnel retain the outer needle 2 in the body of a patient and push down the latch member 8, the engagement between the latch member 8 and the inner needle hub 5 and between the latch member 8 and outer tube 62 is released. As a result, the inner needle hub 5 is moved toward the proximal end of the needle guard 6 by the biasing force of the second elastic body 72 and the outer tube 62 is slid toward the proximal end of the inner tube 61 by the biasing force of the first elastic body 71. At this time, a projection 611 that is provided at the proximal end portion of the inner tube 61 and is projected outwardly further slides toward the distal end of the outer tube 62 while outwardly urging a projection 622 that is provided at the distal end portion of the outer tube 62 and is projected inwardly. As a result, the projection 611 of the inner tube 61 becomes engaged between the projections 621 and 622 provided at the distal end portion of the outer tube 62 as shown in FIGS. 3 and 4 to make the total length of the needle guard 6 maximum so that the inner needle 4 and the inner needle hub 5 are completely protected in the needle guard 6.

The movements of the inner needle hub 5 and the outer tube 62 by the above-mentioned biasing forces take place simultaneously immediately after the latch member 8 is pushed down. Therefore, as compared with a conventional indwelling needle assembly composed of a single elastic body, the inner needle 4 can be accommodated in the needle guard 6 in about half the time in the present invention. Further, as compared with the conventional indwelling needle assembly composed of a single elastic body, the biasing forces of the elastic bodies is small, so that the impact applied to the hand of a user at the time of accommodating the inner needle is reduced.

Figure 5:
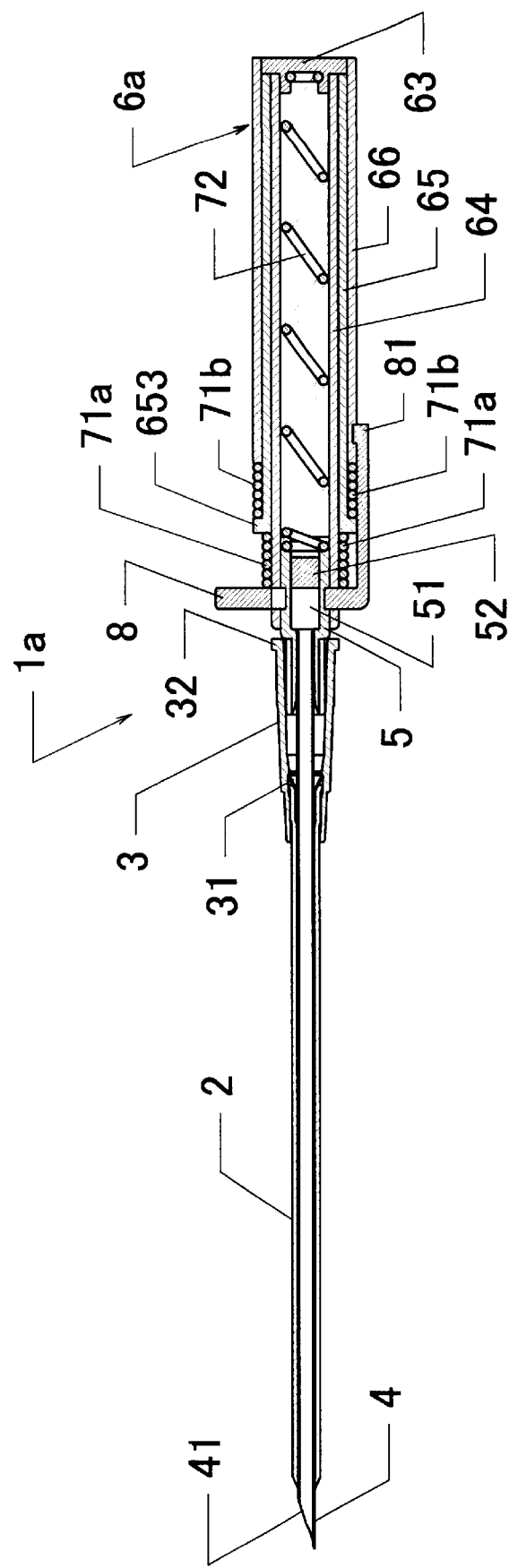
FIG. 5 is a cross-sectional view in the vertical direction of another indwelling needle assembly according to another embodiment of the present invention showing a state before the inner needle is protected.
Figure 6:
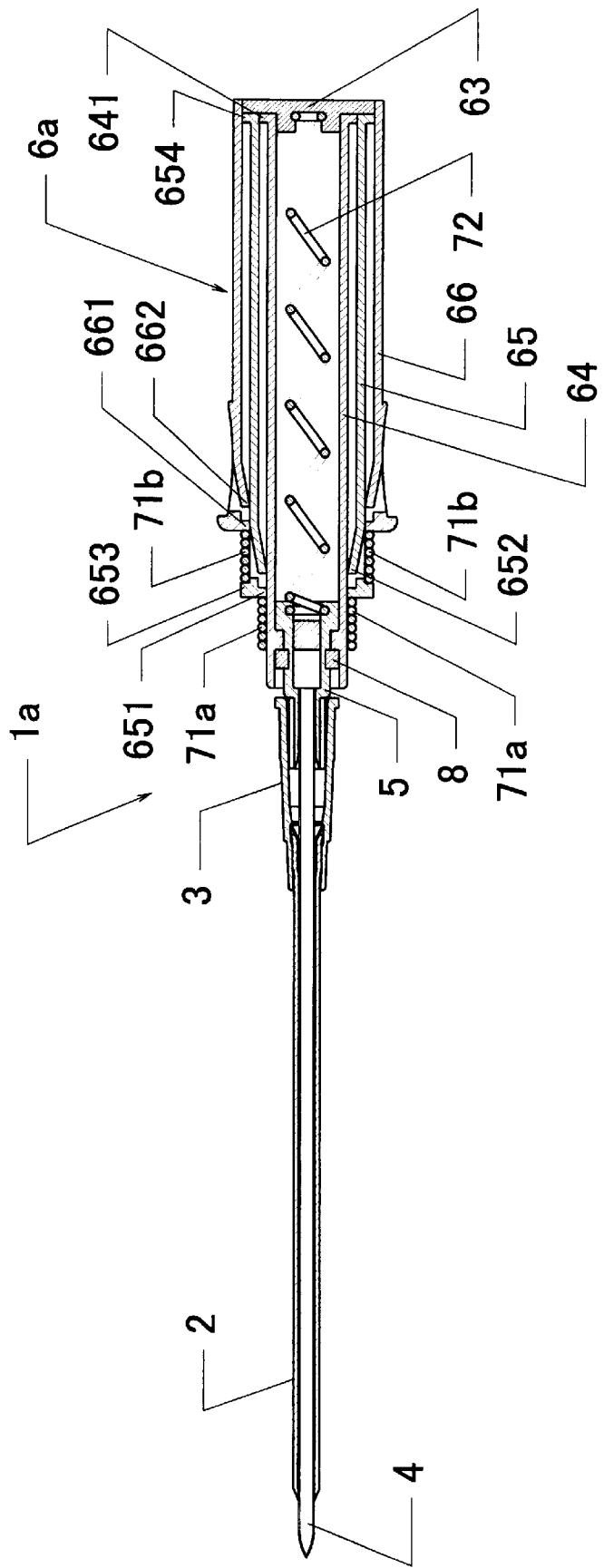
FIG. 6 is a cross-sectional view in the horizontal direction of the indwelling needle assembly shown in FIG. 5.

An embodiment of an indwelling needle assembly 1a in which the needle guard has a triple-tube structure composed of three tubes will be illustrated with reference to FIGS. 5 and 6.

The needle guard 6a has a triple-tube structure composed of three tubes, i.e., tubes 64, 65 and 66, whose diameters increase in the stated order. The tube 64 has an outer diameter slightly smaller than the inner diameter of the tube 65. The tube 65 has an outer diameter slightly smaller than the inner diameter of the tube 66. Each of them is slidable. A cap member 63 is provided at the proximal end portion of the needle guard 6a, which is fitted in or fixed to the proximal end portion of the tube 66, which has the largest diameter. The materials for the tubes 64, 65 and 66 as well as for the cap member 63 may be the same as those for the needle guard 6 described above.

The needle guard 6a is provided with first elastic bodies 71a and 71b as well as a second elastic body 72 for locating the inner needle hub 5 and the inner needle 4 in the needle guard 6a.

The first elastic body 71a is provided on an outer surface of the inner tube 64 and sandwiched between a stopper 8 (cf., FIG. 5) and a projection 651 (cf., FIG. 6) that is provided on the distal end portion of the tube 65 and projects inwardly and urged so that the tube 65 is biased toward the proximal end of the tube 64. Further, the first elastic body 71b is provided on an outer surface of the tube 65, and sandwiched between a projection 653 (cf., FIG. 5) that is provided on the distal end portion of the tube 65 and projects outwardly and a projection 661 (cf., FIG. 6) that is provided on the distal end portion of the outer tube 66 and projects inwardly and urged so that the tube 66 is biased toward the proximal end of the tube 65. The first elastic body 71a may be fixed to the projection 651 and the first elastic body 71b may be fixed to the projection 661, respectively, only at the proximal ends of the first elastic bodies 71a and 71b. The arrangement of the second elastic body 72 is the same as that of the needle guard 6. As the elastic bodies used for the first elastic bodies 71a and 71b as well as for the second elastic body 72, spring steel, elastomers and so forth are used as in the indwelling needle assembly 1 having a double-tube structure. More preferably, spring steel having excellent corrosion resistance is used.

Similarly to the indwelling needle assembly 1 in which the needle guard 6 has a double-tube structure, a stopper 8 such as a latch member is provided on the distal end portion of the needle guard 6a. However, the only difference is that a stopping portion 81 of the latch member 8 is engaged with the tube 66, which has the greatest diameter, so that the needle guard 6a can be held in the state where its total length is shortest against the biasing forces provided by the first elastic bodies 71a and 71b.

When medical personnel push down the latch member 8, the engagement between the latch member 8 and the inner needle hub 5 and between the latch member 8 and the outer tube 66 is released. At this time, the inner needle hub 5 is moved toward the proximal end of the needle guard 6a due to the biasing force of the second elastic body 72; the tube 65 is slid toward the proximal end of the tube 64 due to the biasing force of the first elastic body 71a; and the tube 66 is slid toward the proximal end of the tube 65 due to the biasing force of the first elastic body 71b. When the projection 641 that is provided at the proximal end portion of the tube 64 and projects outwardly is engaged between the projections 651 and 652 that are provided at the distal end portion of the tube 65 and project inwardly and the projection 654 that is provided at the proximal end portion of the tube 65 and projects outwardly is engaged between the projections 661 and 662 that are provided at the distal end portion of the tube 66 and project inwardly, respectively, the total length of the needle guard 6a is the greatest and the inner needle 4 and the inner needle hub 5 are protected in the needle guard 6a.

The movements of the inner needle hub 5 and the tubes 65 and 66 by the above-mentioned biasing forces take place simultaneously immediately after the pushing down of the latch member 8. Therefore, the inner needle 4 can be accommodated in the needle guard 6a in about one third of the time required for a conventional indwelling needle assembly composed of a single elastic body. Further, the impact at the time of accommodating the inner needle is reduced as in the case of the needle guard 6.

EFFECTS OF THE INVENTION

The indwelling needle assembly of the present invention has a multi-tube structure composed of a plurality of telescoping tubes so that the shape of the indwelling needle assembly at the time of use is compact and the inner needle can be accommodated in the needle guard only by pushing down the stopper. As a result, when medical personnel with small hands use the indwelling needle assembly or when using a long indwelling needle such as one retained in a femoral vein of the inguinal region at the time of emergency dialysis, the inner needle can be easily protected using one hand. Furthermore, provision of a first elastic body for elongating the needle guard and of a second elastic body for drawing the inner needle hub in the needle guard result in simultaneous movements of the inner needle hub and tubes toward the proximal end of the assembly due to the biasing forces provided by the elastic bodies. Accordingly, the indwelling needle assembly of the present invention requires a shorter time for accommodating the inner needle in the needle guard as compared with a conventional indwelling needle assembly having only one elastic body, so that there is no fear of being hurt by the distal end of the inner needle or of infection with diseases due to the blood adhered to the inner needle. Further, because a smaller biasing force is required, the impact that the user of the indwelling needle assembly may have at the time of accommodating the inner needle in the needle guard is reduced.

What is claimed is:

1. An indwelling needle assembly comprising an outer needle to pierce and be retained in tissue of a living body; an outer needle hub having a distal end portion to which the outer needle is fixed; an inner needle slidably inserted in a lumen of the outer needle and having a sharp blade edge at a distal end portion thereof; an inner needle hub having a distal end portion to which the inner needle is fixed; a needle guard of a multi-tube structure which comprises a plurality of telescoping tubes and is capable of accommodating the inner needle and the inner needle hub therein; a first elastic means provided on the needle guard for extending the plurality of telescoping tubes so as to lengthen the needle guard; a second elastic means which engages the inner needle hub and is capable of biasing the inner needle hub toward a proximal end side of the needle guard; and a stopper means capable of holding the inner needle hub and the needle guard against biasing forces of the first and second elastic means, respectively.

2. The indwelling needle assembly according to claim 1, wherein the first elastic means is a member provided on circumferential surfaces of a distal end of the plurality of telescoping tubes except for an outermost tube, and urged so as to withdraw one of two adjacent telescoping tubes having a larger diameter toward a proximal end of an other of said two adjacent telescoping tubes having a smaller diameter.

3. The indwelling needle assembly according to claim 1, wherein the second elastic means is a member that is arranged between a cap member provided on a proximal end portion of the needle guard and fixed to an outermost of said plurality of telescoping tubes and a proximal end portion of the inner needle hub and that biases the inner needle hub toward the proximal end of the needle guard.

4. The indwelling needle assembly according to claim 1, wherein the needle guard has a double-tube structure composed of two tubes.

5. The indwelling needle assembly according to claim 1, wherein the needle guard has a triple-tube structure composed of three tubes.

6. The indwelling needle assembly according to claim 1, wherein each of said elastic means comprises spring steel or an elastomer.

* * * * *